United States Patent [19]

Terhune et al.

[11] 4,373,375

[45] Feb. 15, 1983

[54] HYDROGEN SENSOR

[75] Inventors: James H. Terhune; John P. Sturtz; John P. Neissel, all of San Jose, Calif.

[73] Assignee: General Electric Company, San Jose, Calif.

[21] Appl. No.: 218,495

[22] Filed: Dec. 19, 1980

[51] Int. Cl.³ .................. G01N 23/10; G01N 27/66
[52] U.S. Cl. ........................................... 73/19; 73/23
[58] Field of Search .................. 73/23, 19; 250/384; 422/83, 90, 98

[56] References Cited

U.S. PATENT DOCUMENTS

| 2,671,337 | 3/1954 | Hulsberg | 73/23 |
| 2,866,329 | 12/1958 | Hanson | 73/23 |
| 3,923,461 | 12/1975 | Barden | 422/83 |
| 4,143,316 | 3/1979 | Roy et al. | 73/23 |

Primary Examiner—James J. Gill
Attorney, Agent, or Firm—Ivor J. James, Jr.; Samuel E. Turner; Raymond G. Simkins

[57] ABSTRACT

A hydrogen sensing device for determining the concentration of hydrogen in a fluid atmosphere consists of a sealed chamber formed with a window which selectively allows diffusion of hydrogen into the chamber. Alpha particles from a source contained in the chamber ionize the hydrogen and a pair of polarized electrodes collect the resulting electrons to provide a current which is a function of the hydrogen concentration in the chamber. A second window permeable to helium allows escape of the helium from the chamber that is formed by the combination of electrons with alpha particles therein.

28 Claims, 7 Drawing Figures

HYDROGEN SENSOR

BACKGROUND

The invention relates to a device for determining the concentration of hydrogen in a fluid atmosphere. There is a variety of applications for detecting and monitoring the presence of hydrogen. Examples of detecting hydrogen in gaseous atmospheres include smoke detectors, inert coolant atmospheres in transformers, motors and generators and nuclear reactor containment atmospheric monitors.

An example of detecting hydrogen in a liquid includes the measurement of hydrogen in the liquid sodium of a sodium cooled nuclear reactor as a means for detecting water leakage into the sodium from the sodium-water heat exchanger or steam generator.

A number of hydrogen detection arrangements are known. Diffusion cells, based upon the high permeability of certain materials to hydrogen, have been used to concentrate the hydrogen from an atmosphere and apply it to a pressure sensitive sensor such as an ionization gauge, mass spectrograph, Penning gauge or the like to measure the partial pressure of hydrogen in the sensor. Another approach involves the measurement of hydrogen ions in a non-conducting fluid (e.g. pH meters). Still other devices are known which utilize electrochemical reactions to generate a voltage proportional to the hydrogen concentration, such devices being analogous to fuel cells.

Among prior publications concerning detection of gases are the following:

"Ionization Methods for the Analysis of Gases and Vapors" by J. E. Lovelock, Analytical Chemistry, Vol. 33, No. 2, February 1961, pages 162-177. This paper describes various aspects of ionization types of gas detectors.

U.S. Pat. No. 3,683,272 shows a diffusion membrane and ion pump arrangement particularly adapted for detecting hydrogen in liquid sodium.

U.S. Pat. No. 3,866,460 shows apparatus including a hydrogen diffusion membrane and pressure or combustibility measuring means for detecting hydrogen in the liquid coolant of electrical apparatus.

U.S. Pat. No. 3,927,555 shows a palladium alloy tube which undergoes volumetric change as a function of the hydrogen concentration to which it is exposed. A linear variable differential transformer detects the change in the length of the tube as an indication of the hydrogen concentration.

U.S. Pat. No. 3,977,232 shows a diffusion membrane and ion pump arrangement for measuring the concentration of hydrogen in liquid and gaseous environments.

Despite the numerous hydrogen detector arrangements of the prior art, there remains a need for a hydrogen sensor which is small in size and low in cost, is of simple rugged design with long shelf and operating life, has high sensitivity, fast response, is useable over a wide temperature range and in a variety of environments and produces signals compatible with standard electronic circuit designs. It is an object of this invention to provide such a hydrogen sensor.

It is another object to provide a hermetically sealed diffusion cell with a self-contained, long-lived ionization source.

A further object is the provision of means for allowing helium to diffuse out of the cell to thereby improve hydrogen sensitivity.

Another object is a hydrogen sensor cell formed only of inorganic material for operation in high temperature environments.

SUMMARY

These and other objects of the invention are achieved by a hydrogen sensor in the form of a compact, sealed vacuum chamber or cell containing members forming a pair of spaced electrodes connected to a voltage source.

A hydrogen window comprising a membrane formed of a Pd/Ag alloy allows hydrogen to diffuse into the chamber from a surrounding fluid atmosphere. A self-contained radioactive source, such as a layer of an alpha-particle emitting material on the anode, ionizes the hydrogen in the chamber and the resulting electrons collected by the electrodes provide a current flow indicative of the concentration of hydrogen. The current can be processed in a direct current or in a mean-square-voltage mode, the latter providing enhanced signal-to-noise ratio and improved sensitivity by discrimination against leakage currents.

A feature of the invention is the provision of a second window to allow escape from the chamber of helium formed by the combination of electrons with alpha-particles therein. This second window may be formed, for example, of quartz which is permeable to helium. This second window thus allows the helium to diffuse out of and escape from the chamber whereby the relative amount of hydrogen in the chamber, and hence the hydrogen sensitivity of the chamber, is increased.

DRAWING

The invention is described in greater detail with reference to the accompanying drawing including the following figures.

DESCRIPTION

Figure 1:
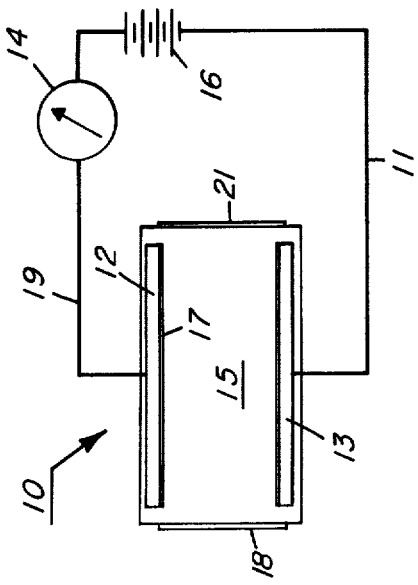
FIG. 1 is a schematic illustration of a basic form of a hydrogen sensor of the invention.

As illustrated in FIG. 1 in basic form, the hydrogen sensor 10 of the invention comprises an evacuated and sealed cell or chamber providing a gas space 15 and containing spaced electrodes, including a cathode 13 and an anode 12 connected by a lead 19 through a current indicator 14 to a source of voltage illustrated as a battery 16. The other terminal of the battery 16 is connected to the cathode 13 by a lead 11. The sensor 10 includes a self-contained source of alpha-particle emitting material illustrated as a layer or coating 17 of radioactive material on the anode 12.

The preferred alpha emitter 17 is Am-241 because of its long half life, the relatively high energy of its alpha particles and its good availability. Other feasible alpha emitters include Ac-227, Pu-238, Np-237, U-234, Th-230. The emitter coating can be applied to the anode in known manner such as by painting, firing, electro-deposition or vacuum deposition.

To allow diffusion of hydrogen from an adjacent atmosphere into the sensor 10 a first window 18 is provided, the window 18 being formed of a thin membrane of a material having high permeability to hydrogen. A preferred hydrogen diffusion membrane material is a palladium alloy such as palladium-silver of 75 percent Pd and 25 percent Ag with a thickness in the order of 0.25 mm.

This hydrogen diffuses through the window 18 into the gas space 15 of the sensor 10 in proportion to the concentration of hydrogen in the adjacent atmosphere. The hydrogen in the space 15 is ionized by the alpha particles emitted from the layer 17 of radioactive material. The resulting electrons are collected at the anode 12 whereby the magnitude of the current flow through lead 19 and indicator 14 is indicative of the concentration of hydrogen in sensor 10 and hence in the adjacent atmosphere.

Some of the electrons combine with the alpha particles to form helium thus, undesirably, forming a current not related to the concentration of hydrogen and hence the sensor accuracy for hydrogen measurement is decreased. To alleviate this situation a second window 21 is provided, the window 21 being formed of a material, such as quartz, which is permeable to helium but not to hydrogen whereby the thus formed helium is allowed to escape from the sensor 10. By this means accuracy of the sensor to hydrogen is increased.

Figure 2:
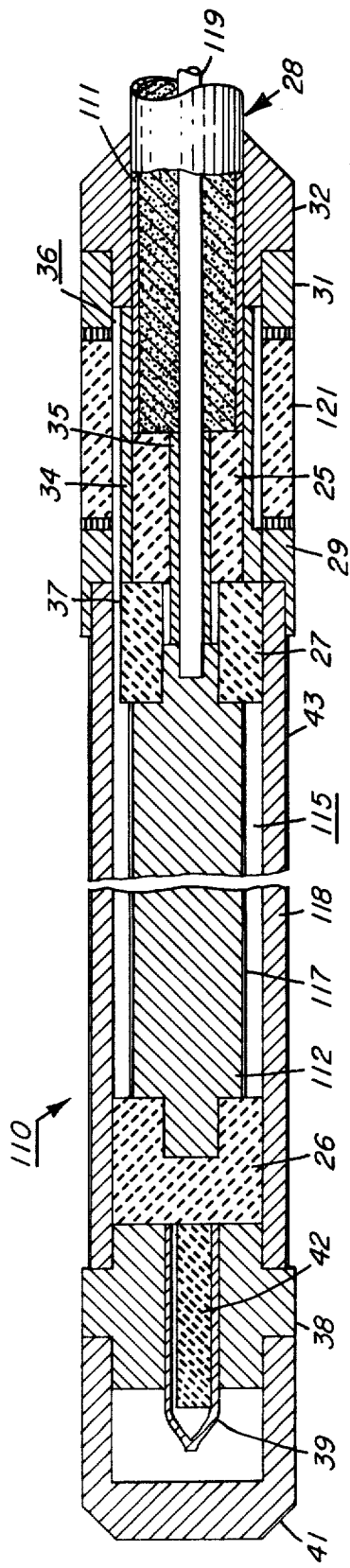
FIG. 2 is a longitudinal cross section view of a preferred form of a hydrogen sensor cell.

A preferred embodiment of a hydrogen sensor 110 according to the invention is illustrated in FIG. 2. Among other reasons, this embodiment is preferred because of its similarity in materials and in construction and processing techniques to well-known neutron detectors as shown, for example, in U.S. Pat. Nos. 3,043,954 and 3,760,183. In other words, its manufacture can be based upon a well-established and proven technology.

The sensor 110 is of cylindrical form, an evacuated and sealed gas space 115 being provided between a cylindrical anode 112 and a tubular hydrogen window 118. Since the hydrogen window 118 is formed of an electrically conductive material such as a palladium-silver alloy, it also serves as the cathode electrode.

The anode 112 is formed with ends of reduced diameter for receiving ceramic support members 26 and 27 by which the anode 112 is supported in spaced relation and electrically insulated from the window 118. The anode 112 is connected to the center conductor 119 of a coaxial cable 28 through an aperture in the support member 27. A layer 117 of alpha-particle emitter material is formed on the large diameter surface of anode 112.

A helium window 121 is formed of a cylinder of quartz sealed in well-known manner to a pair of metallic support rings 29 and 31, the support ring 29 also being sealed to the hydrogen window 118. A metallic cable adapter 32 is connected to the ring 31 and to the outer conductor 111 of the coaxial cable 28 to seal the right-hand end (as shown in FIG. 2) of the assembly. A cylindrical metallic sleeve 34 is connected between the cable adapter 32 and the support ring 29 by which electrical connection is made between the outer conductor 111 of the coaxial cable 28 and cathode/hydrogen window 118. The sleeve 34 is spaced from the helium window 121 to provide a helium gas space 36. The sleeve 34 and support member 27 are formed with flats 37 to provide helium passageways between the gas spaces 115 and 36. The coaxial cable 28 is sealed by a seal insulator 25 bonded between the sleeve 34 and a metallic inner sleeve 35, the sleeve 35 being sealed to the center conductor 119.

At its left-hand end the sensor 110 is sealed by a metallic sleeve 38 connected to the hydrogen window 118 and containing a pumpout tube 39 by which the sensor 110 is evacuated and sealed. A cup-shaped end cover 41 is fitted to the sleeve 38 for protection of the pumpout tube 39. The pumpout tube 39 may contain a loosely fitted ceramic plug 42 to decrease the volume of the inactive gas space in the pumpout tube 39. Minimization of such inactive or stray gas spaces enhances the response time of the sensor.

For some applications of the sensor 110 it is desirable to provide a very thin protective coating 43 on the exterior surface of the hydrogen window 118 to protect it from a hostile environment and/or to passivate the window surface against not yet well-understood surface effects which appear to interfere with the sensitivity and reproducible performance of the sensor. For example for use in liquid sodium, the hydrogen window 118 can be protected by a thin coating of nickel electrodeposited or otherwise plated on the surface thereof in known manner. Other passivating and protective coating materials include alumina, stainless steel, silica, gold, rhodium and rhenium. Annealing the hydrogen window 118 also may be beneficial in suppressing the catalytic surface reactions that compete with the hydrogen permeation process.

In a representative example of the embodiment of the sensor 110 shown in FIG. 2 the anode 112 is formed of stainless steel with a diameter of 5 mm and a length of 25 mm. The alpha particle emitter layer 117 is formed of Am-241 of a thickness of about 0.002 mm. The hydrogen window 118 is formed of 75 percent Pd—25 percent Ag alloy with an inside diameter of 6 mm, a length of 40 mm and a wall thickness of 0.25 mm. The protective and passivating coating 43 is formed of Ni in the order of 1 micron thickness. The helium window 121 is formed of quartz with an inside diameter of 6 mm, a wall thickness of 0.3 mm and a length of 12 mm.

The coaxial cable 28 contains a mineral fill as insulation between the inner conductor 119 and the outer conductor 111 and all parts of the sensor 110 are likewise formed of inorganic material so that the sensor is capable of use in high temperature environments of at least 500° C.

In addition to the hydrogen window surface effects, mentioned hereinbefore, it is found that the sensitivity of the sensor of the invention to hydrogen in a gas mixture is a function of several variables including gas pressure, gas flow, and temperature of the hydrogen window surface. An arrangement for controlling these variables, as shown in FIG. 3, is useful when the sensor is used to monitor, for example, the hydrogen content of the gaseous atmosphere of a nuclear reactor containment.

Figure 3:
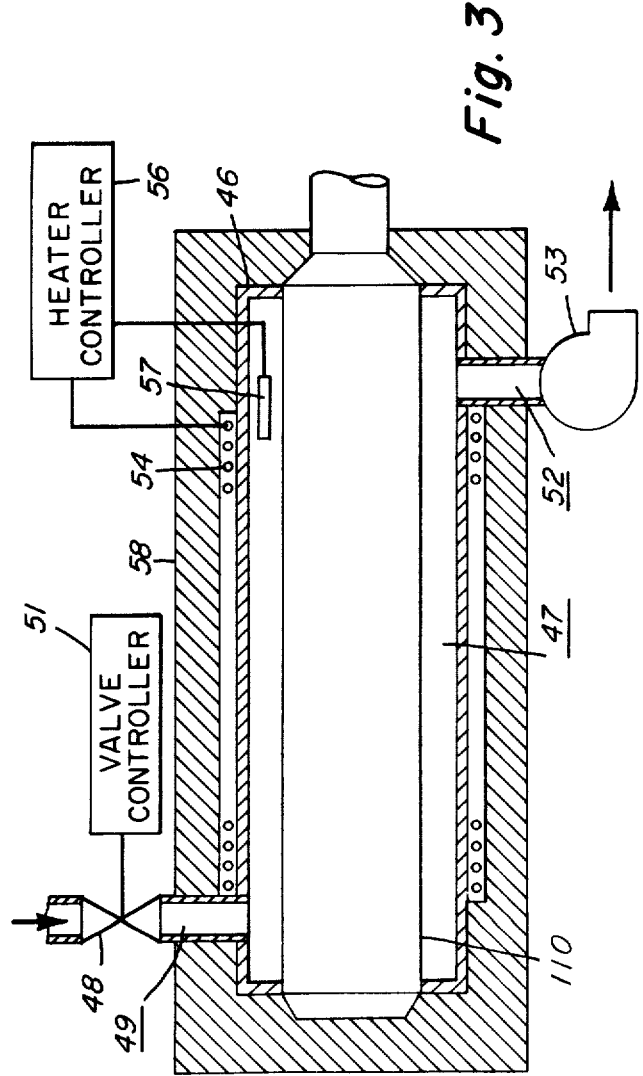
FIG. 3 is a longitudinal cross section view of a heated and insulated container for directing a fluid adjacent a hydrogen sensor cell.

In the arrangement of FIG. 3 the sensor 110 is contained in a vacuum-tight jacket 46 to provide a gas space 47 therebetween. Gas from the atmosphere to be monitored is admitted to the gas space 47 through a flow control valve 48 in an inlet port or conduit 49, the valve 48 being controlled by a suitable valve controller 51. The gas exits the gas space 47 through an outlet port or conduit 52 connected to a pump 53.

To control the temperature in the gas space 47, and hence the temperature of the hydrogen window 118, a heater arrangement is provided. The arrangement includes an electric heating coil 54 wrapped around the jacket 46 and powered from a heater controller 56, the temperature in the gas space 47 being sensed by, for example, a thermocouple 57. The jacket 46 and heating coil 54 are encased in an enclosure 58 of suitable heat insulating material, e.g, glass fiber.

Thus the arrangement of FIG. 3 provides for control of the variables gas pressure, temperature and gas flow. For monitoring ambient air for abnormal hydrogen content these variables may be controlled, for example, as follows: the pump 53 is selected or controlled to provide a pressure in the gas space 47 of up to about 70 cm Hg absolute with 20 being a preferred value. The temperature is held substantially constant in the range of about 200° C. to 700° C. with 250° found to be a practical operating temperature. The gas flow through the gas space 47, as controlled by valve 48, may be a constant or a pulsed flow, the latter being preferred because it provides enhanced repeatability of sensor response. Thus the valve 48 controls the gas inlet flow over a range, for example, of 500 to 2400 ccm. For constant flow a preferred flow rate is about 1500 ccm. For pulsed flow the valve 48 is periodically actuated to provide alternate periods of flow and no flow or (by closing valve 48) pumpout to a negative pressure. The flow rate may be varied along with flow duration. Example flow rates are 500 ccm for periods of 1 second and 2000 ccm for periods of 8 seconds.

In the elementary form of the invention illustrated in FIG. 1 the output signal from the sensor 10 is a current through indicator 14 which is a function of the hydrogen concentration in the gas space 15. Thus the indicator 14 can be calibrated to display the hydrogen concentration.

In a practical system it is usually a practical necessity to amplify the sensor output signal and usually desirable to convert the current signal to a voltage signal for compatibility with amplifying, processing, display and recording devices.

Figure 4:
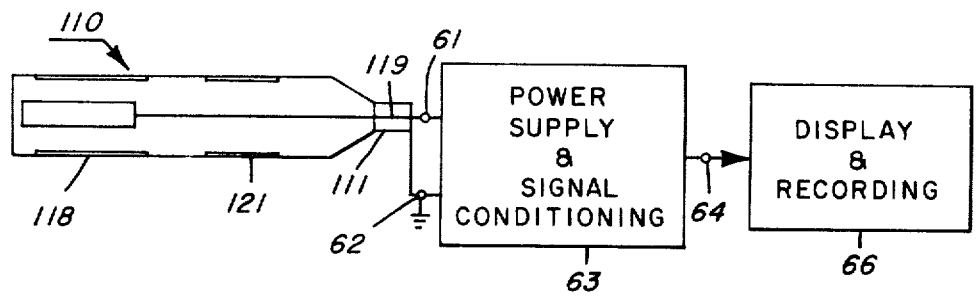
FIG. 4 is a schematic illustration of the sensor cell and a block diagram of circuits for receiving the signals therefrom.

Processing of the signal from the sensor 110 (FIG. 2) is illustrated in block diagram form in FIG. 4. The center and outer conductors 119 and 111 of the coaxial output cable 28 of sensor 110 are connected to a pair of input terminals 61 and 62 (terminal 62 being a common or grounded terminal) of a power supply and signal conditioning circuit 63. (Embodiments of circuits 63 are shown in FIGS. 5 and 6 discussed hereinafter.)

The conditioned signal from circuit 63 is applied through a terminal 64 to appropriate display and/or recording devices 66. Appropriate such devices can be selected from a variety of well-known forms thereof such as digital or analog voltmeters for visual display, strip or chart recorders for visual recording and digital or analog recording for storage.

Figure 7:
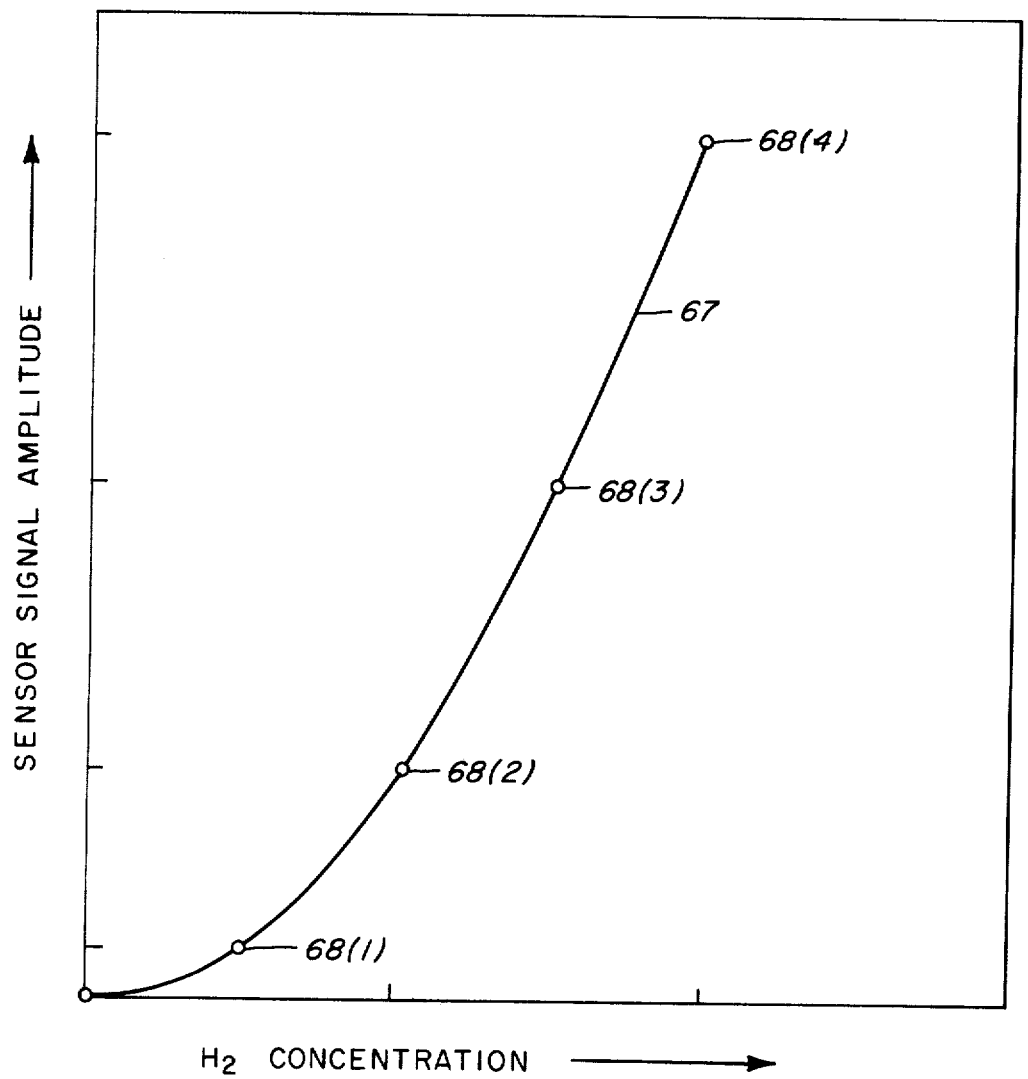
FIG. 7 illustrates a typical sensor signal amplitude versus hydrogen concentration response curve.

To be noted is that the signal from the hydrogen sensor typically is not a linear function of the hydrogen concentration. A representative response curve of sensor signal amplitude versus hydrogen concentration is illustrated as a curve 67 in FIG. 7. Such a response curve can be generated, for example, by successively exposing the sensor to a plurality of samples of gas containing different known concentrations of hydrogen over the range of hydrogen concentrations of interest. (Preferably the gas composition is otherwise similar to that of the atmosphere in which the sensor is to be used.) The sensor signal amplitude for each concentration is measured and from these signals the response curve can be generated by mathematical or graphic interpolation in known manner, for example, by plotting the response points, such as points 68(1) to 68(4) of FIG. 7, and fitting a curve thereto. From such a response curve (or the mathematical expression thereof) the display and recording devices 66 (FIG. 4) can be calibrated appropriately.

Figure 5:
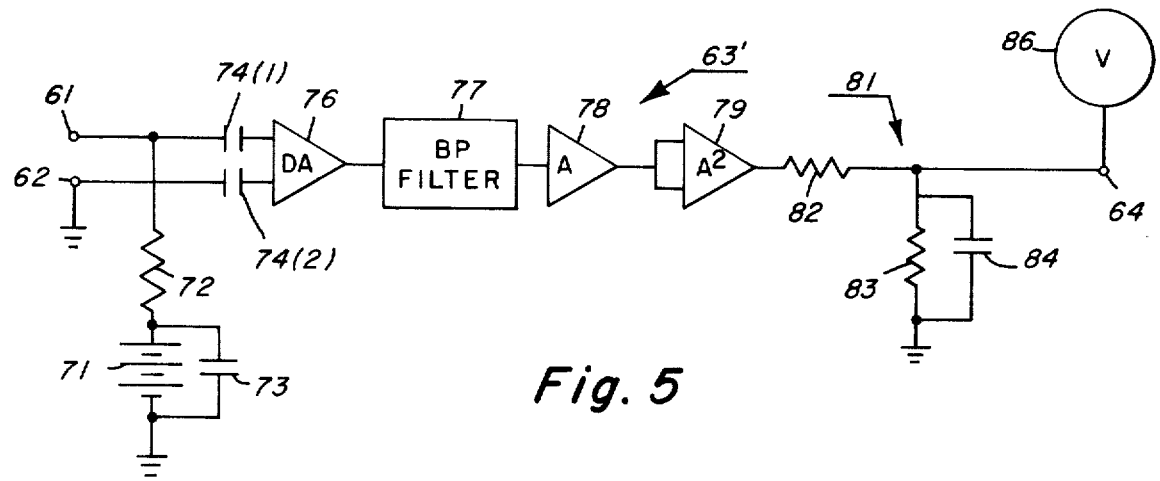
FIG. 5 is a schematic illustration of a power supply and signal conditioning circuit.
Figure 6:
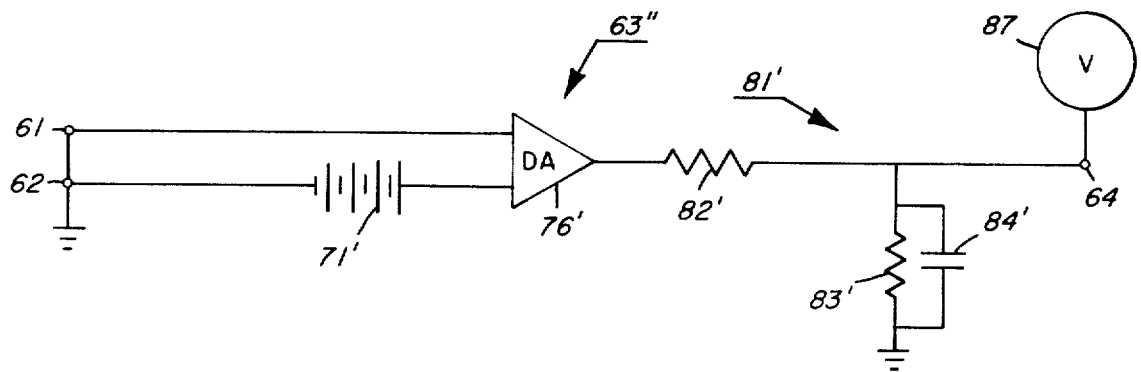
FIG. 6 is a schematic illustration of an alternate embodiment of a power supply and signal conditioning circuit.

As mentioned above, alternate embodiments of power supply and signal conditioning circuits (63 of FIG. 4) are shown in FIGS. 5 and 6. Preliminary to the discussion of these circuits, it is pointed out that the signal from the sensor 110 includes both alternating and direct current components because of the random nature of the alpha-particle radiation from layer 117 and the consequent hydrogen ionization events. The alternating current component covers a band of frequencies with a frequency spectrum that is substantially flat from zero to a half-power point determined by the ion collection time of the sensor.

Since the amplitude of the alternating current component (as well as the amplitude of the direct current component) is a function of the hydrogen concentration in the sensor chamber, the alternating current component can be used as the sensor output signal. The advantage of such use is that leakage currents and signals from gamma radiation are rejected.

A power supply and signal conditioning circuit 63′ which utilizes the alternating component of the sensor signal is illustrated in FIG. 5. The power supply portion is illustrated as a battery 71 connected to the sensor electrodes, through a sensor load and current limiting resistor 72, through terminals 61 and 62. A capacitor 73 bypasses the alternating current signal around the battery 71. The alternating current voltage developed across resistor 72 is applied through a pair of coupling capacitors 74(1) and 74(2) to a differential amplifier 76 (e.g. a Fairchild model No. UA749C).

The signal from amplifier 76 is applied to a bandpass filter 77 (e.g. T. T. Electronics Inc. model No. K8777-B) selected to pass the desired portion of the sensor signal but to reject high and low frequency signals. An amplifier 78 receives the output signal from the bandpass filter 77 and its output signal is supplied to a squaring circuit 79 (e.g. Analogue Devices, Inc. model No. 429B). The output of squaring circuit 79 is connected to output terminal 64 through an averaging or smoothing RC circuit 81—including a series resistor 82 and shunt connected resistor 83, and capacitor 84.

Thus the action of the squaring circuit 79 and averaging circuit 81 provides an output signal on terminal 64 that is proportioned to the mean-square alternating current component of the sensor signal. As discussed hereinbefore, the output signal on terminal 64 is supplied to suitable display and/or recording devices, illustrated in FIG. 5 as a voltmeter 86.

A power supply and signal conditioning circuit 63″ which utilizes the direct current component of the sensor signal is illustrated in FIG. 6. In this circuit an input terminal of a differential amplifier 76′ is connected to terminal 61 to receive the sensor output signal while the other terminal of the differential amplifier 76′ is connected through a power supply, illustrated as a battery 71′, to the common or grounded input terminal 62. The amplified signal is applied to an averaging or smoothing RC circuit 81' (including resistors 82' and 83' and capacitor 84') to provide a circuit output signal to terminal 64 which is proportional to the direct current component of the sensor signal averaged over a period determined by the time constant of the RC circuit 81'. A suitably calibrated direct current (DC) voltmeter 87 can be provided to visually indicate the amplitude of the signal on terminal 64.

Signal processing circuits similar to those illustrated herein in FIGS. 4, 5 and 6 are shown and described in U.S. Pat. No. 4,103,166 which is incorporated herein by reference.

What is claimed is:

1. A hydrogen sensor comprising: a sealed and evacuated chamber; a first window in said chamber formed of a material selectively permeable to hydrogen to admit hydrogen from an adjacent atmosphere into said chamber; a source of alpha particles in said chamber for ionizing the hydrogen therein; a second window in said chamber formed of a material selectively permeable to helium, said second window providing an outlet from said chamber for helium formed by combination of alpha particles and electrons in said chamber; and a pair of spaced electrodes in said chamber connected to a source of voltage for collecting electrons in said chamber, the resulting electron current being indicative of the concentration of hydrogen in said chamber.

2. The sensor of claim 1 wherein said first window is formed of a palladium-silver alloy.

3. The sensor of claim 1 wherein the outer surface of said first window is covered with a coating of a material selected from the group nickel, stainless steel, alumina, silica, gold, rhodium and rhenium for protection of the surface of said first window but sufficiently thin to permit diffusion of hydrogen through said first window.

4. The sensor of claim 1 wherein said alpha emitter is selected from the group Am-241, Ac-227, Pu-238, Np-237, U-234 and Th-230.

5. The sensor of claim 1 wherein said alpha emitter is formed of Am-241.

6. The combination of claim 1 including means for maintaining said sensor within a predetermined temperature range.

7. The combination of claim 6 wherein said temperature range is from 200 to 700 degrees C.

8. The sensor of claim 1 wherein all the components of said sensor are formed of inorganic materials whereby said sensor is adapted for use in high temperature environments.

9. The combination of claim 1 further including a container surrounding said sensor and forming an enclosed fluid space adjacent said sensor and means for directing a fluid to be sensed for hydrogen content through said container.

10. The combination of claim 9 including means for heating said fluid space.

11. The combination of claim 10 including means for maintaining said fluid space within a predetermined temperature range.

12. The combination of claim 11 wherein said temperature range is from 100 to 650 degrees C.

13. The combination of claim 10 including a jacket of heat insulation material around said container.

14. The combination of claim 9 wherein said means for directing a fluid through said container provides a pressure less than atmospheric pressure in said container.

15. The combination of claim 9 wherein said means for directing a fluid through said container provides a substantially constant rate of flow of fluid through said container.

16. The combination of claim 9 wherein said means for directing a fluid through said container provides a periodically varying rate of flow of fluid through said container.

17. The combination of claim 16 wherein said periodically varying rate of flow of fluid through said container comprises alternating periods of no flow and flow at flow rates of from about 500 ccm for between 1 and 8 seconds to about 2000 ccm for between 2 and 8 seconds.

18. The combination of claim 1 further including means for processing said resulting electron current, comprising: means for applying only the alternating component of said electron current to a bandpass filter, said filter substantially rejecting signals higher and lower in frequency than a desired band of frequencies.

19. The combination of claim 18 further including a signal squaring circuit connected to receive signals from said bandpass filter and an averaging circuit connected between said squaring circuit and an output terminal whereby the signal at said output terminal is proportional to the mean-square of the alternating current component of said electron current.

20. The combination of claim 1 further including an amplifier circuit for receiving and amplifying said resulting electron current, an averaging RC circuit connecting the output of said amplifier circuit and an output terminal whereby the signal at said output terminal is proportional to the direct current component of said electron current averaged over a period determined by the time constant of said RC circuit.

21. A device for sensing the hydrogen concentration in a fluid atmosphere, comprising: a first tubular member formed of an electrically conductive material which is selectively permeable to hydrogen; a second tubular member formed of a material which is selectively permeable to helium secured in end-to-end relationship to said first tubular member to form therewith a tubular body; a cylindrical member formed at least with an electrically conductive surface electrically insulated from and coaxially positioned with respect to said first tubular member to form therewith an annular chamber for receiving hydrogen which diffuses from said atmosphere through said first tubular member; a coaxial cable sealed in one end of said tubular body, the center conductor of said coaxial cable being electrically connected to said electrically conductive surface of said cylindrical member and the outer conductor of said coaxial cable being electrically connected to said first tubular member; means for sealing the other end of said body; a source of alpha particles contained in said chamber for ionizing hydrogen therein, said first tubular member and said conductive surface of said cylindrical member serving as electrodes to collect the resulting electrons; and gas passage means communicating said chamber with the inside surface of said second tubular member to provide escape of helium from said chamber.

22. The device of claim 21 wherein said first tubular member is formed of a palladium-silver alloy.

23. The device of claim 22 wherein the outer surface of said first tubular member is covered with a coating of material selected from the group nickel, stainless steel, alumina, silica, gold, rhodium and rhenium—for protection of said surface but sufficiently thin to permit diffusion of hydrogen through said first tubular member.

24. The device of claim 21 wherein said source of alpha particles is a material selected from the group AM-241, Ac-227, Pu-238, Np-237, U-234, Th-230.

25. The device of claim 21 wherein said source of alpha particles is formed of Am-241.

26. The device of claim 21, wherein said source of alpha particles is an alpha emitting material coated on the surface of said cylindrical member.

27. The device of claim 21 wherein said means for sealing the other end of said body includes a pump-out tube for evacuating said body.

28. The device of claim 21 wherein all of the components of said device are formed of inorganic materials whereby said device is adapted for use in high temperature environments.

* * * * *